United States Patent [19]

Evans et al.

[11] 3,962,452

[45] June 8, 1976

[54] BENZOXAZOLE DERIVATIVES AS THERAPEUTICS

[75] Inventors: Delme Evans, Chalfont St. Peter; David William Dunwell, Camberley; Terence Alan Hicks, Farnborough, all of England

[73] Assignee: Lilly Industries, Ltd., London, England

[22] Filed: June 17, 1975

[21] Appl. No.: 587,562

Related U.S. Application Data

[62] Division of Ser. No. 356,251, May 5, 1973, Pat. No. 3,912,748.

[30] Foreign Application Priority Data

May 18, 1972 United Kingdom............... 23409/72

[52] U.S. Cl................................ 424/272; 424/250; 424/263
[51] Int. Cl.² ................ A61K 31/42; A61K/31/44; A61K 31/495

[58] Field of Search..................... 424/272, 250, 263

[56] References Cited

UNITED STATES PATENTS 3,136,773   6/1964   Maeder et a....................... 260/307

*Primary Examiner*—Stanley J. Friedman
*Attorney, Agent, or Firm*—James L. Rowe; Everet F. Smith

[57] ABSTRACT

The invention provides novel 5- and 6-benzoxazolyl alkanoic acids, optionally substituted in the 2-position, and derivatives thereof which possess anti-inflammatory, anti-pyretic and analgesic activity. Also provided is a process for preparing such compounds by cyclising an appropriately substituted o-aminophenol and, if necessary, converting the resultant benzoxazole to the desired compound.

3 Claims, No Drawings

BENZOXAZOLE DERIVATIVES AS THERAPEUTICS

This is a div. of appl. Ser. No. 356,251 filed May 5, 1973 now U.S. Pat. No. 3,912,748, issued Oct. 14, 1975.

This invention relates to certain new benzoxazole derivatives which have been found to possess valuable pharmacological activity or are useful as intermediates for preparing such active compounds and to a process by which such compounds may be prepared. The invention also includes pharmaceutical compositions containing said pharmacologically active compounds and a method of treating animals including humans comprising administering thereto an effective dose of said compounds or compositions. The invention also provides novel intermediates from which the benzoxazole derivatives of the present invention may be prepared.

According to the present invention therefore, there are provided novel benzoxazole derivatives of the formula:

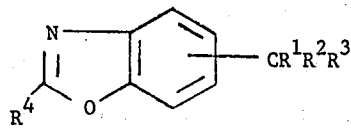

I wherein the group $-CR^1R^2R^3$ is in the 5- or 6-position of the benzoxazole nucleus, $R^1$ and $R^2$ are independently hydrogen or $C_{1-6}$ alkyl, $R^3$ is a nitrile group, carboxy or a salt, ester, amide or hydroxamic acid derivative thereof, or hydroxymethyl or an ester thereof, and $R^4$ is hydrogen, hydroxy, amino, $C_{2-7}$ acylamino, $C_{1-6}$ alkyl, cyclohexyl, or a heteroaryl or phenyl group optionally substituted in any available position by one or more $C_{1-6}$ alkylsulphonyl, halogen, $C_{1-6}$ alkyl, $C_{1-6}$ alkoxy, $C_{1-6}$ haloalkyl, nitro, $C_{2-7}$ acyl, hydroxy, amino, $C_{1-6}$ alkylamino, or $C_{2-7}$ acylamino or optionally substituted in two adjacent positions by methylene- or ethylene-dioxy.

The term "$C_{1-6}$ alkyl" as used herein means a straight or branched chain alkyl group containing from 1 to 6 carbon atoms such as methyl, ethyl, isopropyl, n-butyl, s-butyl, t-butyl, n-amyl, s-amyl, n-hexyl, 2-ethylbutyl and 4-methylamyl. Similarly the terms "$C_{1-6}$ alkoxy", "$C_{1-6}$ alkylsulphonyl", "$C_{1-6}$ alkylamino", "$C_{2-7}$ acyl", and "$C_{2-7}$ acylamino" mean the aforementioned $C_{1-6}$ alkyl groups linking through an oxygen atom, or an $-SO_2-$, $-NH-$, $-CO-$ or $-CONH-$ group respectively. The term "$C_{1-6}$ haloalkyl" as used herein means the aforementioned $C_{1-6}$ alkyl groups substituted by one or more halogen atoms such as, for example, chloromethyl, bromomethyl, trifluoromethyl, 2-chloroethyl, pentafluoroethyl, 3-bromopropyl, 2-chlorobutyl, 4-bromobutyl, 2-(2-chloroethyl)-3-chloropropyl and 6-chlorohexyl. The term "heteroaryl" as used herein means a heterocyclic aromatic group containing at least one ring atom which is not carbon, preferred examples of which are 5- or 6-membered heterocyclic aromatic rings containing one or two ring atoms selected from oxygen, sulphur and nitrogen.

Within the aforementioned group of compounds of formula I, there is a sub-group preferred for the ease of availability of the necessary starting materials, which sub-group comprises compounds wherein the group $-CR^1R^2R^3$ is in the 5- or 6-position of the benzoxazole nucleus, $R^4$ is hydrogen, hydroxy, amino, $C_{1-4}$ alkyl, cyclohexyl, furyl, thienyl, pyridyl, pyrazinyl, or a phenyl group optionally substituted in any available position by one or two groups selected from halogen, nitro, amino, hydroxy, $C_{1-4}$ alkyl, $C_{1-4}$ alkoxy, $C_{2-4}$ acyl, $C_{1-4}$ alkylsulphonyl, trifluoromethyl, pentafluoroethyl, $C_{1-4}$-monohalalkyl or optionally substitued in two adjacent positions by methylene- or ethylene-dioxy, $R^1$ and $R^2$ are independently hydrogen, methyl or ethyl, and $R^3$ is:

i. the group $-COOR^5$, where $R^5$ is $C_{1-4}$ alkyl, amino-$C_{1-4}$ alkyl, $C_{1-4}$ alkylamino-$C_{1-4}$ alkyl or di-$C_{1-4}$ alkylamino-$C_{1-4}$ alkyl; or ii. the group $-CO-R^6$ where $R^6$ is $-NHOH$ or $-NR^7R^8$ where $R^7$ and $R^8$ are independently hydrogen or $C_{1-4}$ alkyl; or iii. the group $-CH_2OR^9$ where $R^9$ is hydrogen or $C_{1-4}$ alkyl; or iv. the group $-COOH$ or an alkali or alkaline earth metal, aluminium or ammonium salt thereof; or v. a nitrile group.

Using standard test procedures in animals, compounds of the foregoing type have been assessed for pharmacological activity and lack of toxicity. Such tests have revealed a further group of compounds in which the combination of high activity, especially anti-inflammatory activity, and low toxicity is most marked. This especially useful group of compounds fall within the general formula:

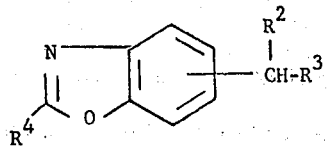

II wherein the group

is in the 5- or 6-position of the benzoxazole nucleus, $R^4$ is a phenyl group optionally substituted by one or two groups selected from halogen, trifluoromethyl, methyl, methoxy, acetyl, methylsulphonyl, nitro or hydroxy, $R^2$ is hydrogen or most advantageously methyl, and $R^3$ is as defined in parts (i) to (iv) above, especially parts (i) and (iv).

Examples which may be given of the compounds of this invention are:
5-benzoxazolyl acetic acid
5-benzoxazolyl acetonitrile
2-(5-benzoxazolyl) propionic acid
2-(5-benzoxazolyl) propionitrile
2-(5-benzoxazolyl) butyric acid
2-methyl-2-(5-benzoxazolyl) propionic acid
2-(6-benzoxazolyl) propionic acid
2-(6-benzoxazolyl) propionitrile
2-(6-benzoxazolyl) butyric acid
2-(6-benzoxazolyl) isobutyric acid
sodium 2-(6-benzoxazolyl) propionate
ethyl 6-benzoxazolyl acetate
diethylaminoethyl 2-(5-benzoxazolyl) propionate
5-benzoxazolyl acetamide N,N-dimethyl 6-benzoxazolylpropionamide
2-(5-benzoxazolyl) propionylhydroxamic acid
2-hydroxy-5-benzoxazolyl acetic acid
2-(2-hydroxy-6-benzoxazolyl) propionic acid
2-(2-methyl-6-benzoxazolyl) butyric acid
ethyl 2-(2-t-butyl-5-benzoxazolyl) propionate
2-(2-isopropyl-5-benzoxazolyl) propionamide
2-(5-benzoxazolyl) propyl alcohol
2-(2-n-butyl-6-benzoxazolyl) propionic acid
2-cyclohexyl-5-benzoxazolyl acetic acid
2-cyclohexyl-5-benzoxazolyl acetonitrile
2-cyclohexyl-6-benzoxazolyl acetic acid
methyl 2-(2-cyclohexyl-5-benzoxazolyl) propionate
dimethylaminoethyl 2-cyclohexyl-5-benzoxazolyl acetate
potassium 2-(2-cyclohexyl-5-benzoxazolyl) butyric acid
2-(2-amino-6-benzoxazolyl) propyl alcohol
2-(2-amino-5-benzoxazolyl) propionic acid
2-amino-5-benzoxazolyl acethydroxamic acid
2-[2-(fur-2-yl)-5-benzoxazolyl]-2-methylpropionic acid
2-[2-(fur-2-yl)-6-benzoxazolyl] propionic acid
t-butyl 2(fur-2-yl)-5-benzoxazolyl acetate
2-[2-(fur-3-yl)-5-benzoxazolyl] ethanol
2-[2-(fur-2-yl)-5-benzoxazolyl] propionitrile
2-[2-(thien-2-yl)-5-benzoxazolyl] propyl alcohol
2-[2-(thien-2-yl)-6-benzoxazolyl]-2-ethyl propionic acid
ethyl 2-(thien-3-yl)-5-benzoxazolyl acetate
2-(thien-3-yl)-5-benzoxazolyl acethydroxamic acid
2-(pyrid-4-yl)-5-benzoxazolyl acetic acid
2-(pyrid-2-yl)-6-benzoxazolyl acetonitrile
2-[2-(pyrid-2-yl)-5-benzoxazolyl] propionic acid
isopropyl 2-[2-(pyrid-2-yl)-6-benzoxazolyl] propionate
2-[2-(pyrid-2-yl)-6-benzoxazolyl] propyl alcohol
2-(pyrazin-2-yl)-6-benzoxazolyl acetic acid
2-(pyrazin-2-yl)-6-benzoxazolyl ethyl alcohol
2-[2-(pyrazin-2yl)-5-benzoxazolyl] propionic acid
ethyl 2-[2-(pyrazin-2-yl)-5-benzoxazolyl] propionate
2-[2-(4-chlorophenyl)-5-and 6-benzoxazolyl] propionitrile
2-(4-nitrophenyl)-5-benzoxazolyl acetic acid
2-(4-aminophenyl)-6-benzoxazolyl acetic acid
ethyl 2-[2-(3,4-methylenedioxyphenyl)-5-benzoaxazolyl] propionate
2-[2-(4-β-chloroethylphenyl)-6-benzoxazolyl] propionic acid
2-[2-(3,4-diethylphenyl)-5-benzoxazolyl] propionic acid
2-(3-ethoxyphenyl)-5-benzoxazolyl acethydroxamic acid
2-(4-hydroxyphenyl)-6-benzoxazolyl ethanol
ethyl 2-(4-dimethylaminophenyl)-5-benzoxazolyl acetate
2-(3,4-dihydroxyphenyl)-5-benzoxazolyl acetic acid
2-[2-(4-t-butoxyphenyl)-6-benzoxazolyl] butyric acid
2-[2-(4-chlorophenyl)-5-benzoxazolyl] butyronitrile
diethylaminoethyl 2-(2-methoxyphenyl)-5-benzoxazolyl acetate
2-[2-(2,4-dinitrophenyl)-5-benzoxazolyl] propyl alcohol
2-[2-(4-aminophenyl)-6-benzoxazolyl] propionylhydroxamic acid
sodium 2-(4-n-butylphenyl)-5-benzoxazolyl acetate Examples of preferred compounds of the present invention are:
A (i) 2-phenyl-5- and 6-benzoxazolyl acetic acid
2-(4-chlorophenyl)-5- and 6-benzoxazolyl acetic acid
2-(4-methylphenyl)-5- and 6-benzoxazolyl acetic acid
2-(4-trifluoromethylphenyl)-5- and 6-benzoxazolyl acetic acid
2-(4-methoxyphenyl)-5- and 6-benzoxazolyl acetic acid
2-(4-bromophenyl)-5- and 6-benzoxazolyl acetic acid
2-(4-fluorophenyl)-5- and 6-benzoxazolyl acetic acid
2-(3-chlorophenyl)-5- and 6-benzoxazolyl acetic acid
2-(3-methylphenyl)-5- and 6-benzoxazolyl acetic acid
2-(3-trifluromethylphenyl)-5- and 6-benzoxazolyl acetic acid
2-(3,4-dichlorophenyl)-5- and 6-benzoxazolyl acetic acid
2-(2-methylphenyl)-5- and 6-benzoxazolyl acetic acid
2-(2-chlorophenyl)-5- and 6-benzoxazolyl acetic acid
2-(2-methoxyphenyl)-5- and 6-benzoxazolyl acetic acid
2-(3,4-dimethylphenyl)-5- and 6-benzoxazolyl acetic acid
A(ii) the sodium, potassium, aluminium and ammonium salts of the acids of A(i) above,
A(iii) the $C_{1-4}$ alkyl, amino-$C_{1-4}$ alkyl, dimethylamino-$C_{1-4}$ alkyl and diethylamino-$C_{1-4}$ alkyl esters of the acids of A(i) above,
B. 2-phenyl-5- and 6-benzoxazolyl acetamide
2-phenyl-5- and 6-benzoxazolyl acethydroxamic acid
2-(4-chlorophenyl)-5- and 6-benzoxazolyl acethydroxamic acid
2-(4-chlorophenyl)-5- and 6-benzoxazolyl acetamide
2-(4-bromophenyl)-5- and 6-benzoxazolyl acetamide
2-(4-fluorophenyl)-5- and 6-benzoxazolyl acetamide
2-(4-methylphenyl)-5- and 6-benzoxazolyl acetamide
2-(4-methoxyphenyl)-5- and 6-benzoxazolyl acetamide
2-(2-methoxyphenyl)-5- and 6-benzoxazolyl acetamide
2-(2-chlorophenyl)-5- and 6-benzoxazolyl acetamide
2-(3,4-dichlorophenyl)-5- and 6-benzoxazolyl acetamide
2-(3-chlorophenyl)-5- and 6-benzoxazolyl acetamide
2-(3-methylphenyl)-5- and 6-benzoxazolyl acetamide
2-(4-trifluoromethylphenyl)-5- and 6-benzoxazolyl acetamide
2-(4-trifluoromethylphenyl)-5- and 6-benzoxazolyl acethydroxamic acid
2-(4-bromophenyl)-5- and 6-benzoxazolyl acethydroxamic acid
2-(4-fluorophenyl)-5- and 6-benzoxazolyl acethydroxamic acid
2-(3,4-dimethylphenyl)-5- and 6-benzoxazolyl acethydroxamic acid
2-(4-methoxyphenyl)-5- and 6-benzoxazolyl acethydroxamic acid
2-(4-methylphenyl)-5-and 6-benzoxazolyl acethydroxamic acid 2-(3-chlorophenyl)-5-and 6-benzoxazolyl acethydroxamic acid
2-[2-(3-chlorophenyl)-5-and 6-benzoxazolyl] propionylhydroxamic acid
2-[2-(4-chlorophenyl)-5-and 6-benzoxazolyl] propionylhydroxamic acid
2-[2-(2-chlorophenyl)-5-and 6-benzoxazolyl] propionylhydroxamic acid
2-[2-(3,4-dichlorophenyl)-5-and 6-benzoxazolyl] propionylhydroxamic acid
2-[2-(4-trifluoromethylphenyl)-5-and 6-benzoxazolyl] propionylhydroxamic acid
2-[2-(4-methylphenyl)-5-and 6-benzoxazolyl] propionylhydroxamic acid
2-[2-(4-methyoxyphenyl)-5-and 6-benzoxazolyl] propionylhydroxamic acid
2-[2-(3-methoxyphenyl)-5-and 6-benzoxazolyl] propionamide
2-[2-(4-methylphenyl-5-and 6-benzoxazolyl] propionamide
2-[2-(4-trifluoromethylphenyl)-5-and 6-benzoxazolyl] propionamide
2-[2-(4-methyoxyphenyl)-5-and 6-benzoxazolyl] propionamide
2-[2-(4-chlorophenyl)-5-and 6-benzoxazolyl] propionamide
2-[2-(4-bromophenyl)-5-and 6-benzoxazolyl] propionamide
2-[2-(4-fluorophenyl)-5-and 6-benzoxazolyl] propionamide (i) 2-phenyl-5-and 6-benzoxazolyl ethanol
2-(4-chlorophenyl)-5-and 6-benzoxazolyl ethanol
2-(4-methylphenyl)-5-and 6-benzoxazolyl ethanol
2-(4-trifluoromethylphenyl)-5-and 6-benzoxazolyl ethanol
2-(4-methoxyphenyl)-5-and 6-benzoxazolyl ethanol
2-(4-bromophenyl)-5-and 6-benzoxazolyl ethanol
2-(4-fluorophenyl)-5-and 6-benzoxazolyl ethanol
2-(3-chlorophenyl)-5-and 6-benzoxazolyl ethanol
2-(3-methylphenyl)-5-and 6-benzoxazolyl ethanol
2-(3,4-dichlorophenyl)-5-and 6-benzoxazolyl ethanol
2-(2-methylphenyl)-5-and 6-benzoxazolyl ethanol
2-(2-methoxyphenyl)-5-and 6-benzoxazolyl ethanol
2-(2-chlorophenyl)-5-and 6-benzoxazolyl ethanol
2-[2-(2-chlorophenyl)-5-and 6-benzoxazolyl] propyl alcohol
2-[2-(3-chlorophenyl)-5-and 6-benzoxazolyl] propyl alcohol
2-[2-(4-chlorolphenyl)-5-and 6-benzoxazolyl] propyl alcohol
2-[2-(3,4-dichlorophenyl)-5-and 6-benzoxazolyl] propyl alcohol
2-[2-(3,4-dimethylphenyl)-5-and 6-benzoxazolyl] propyl alcohol
2-[2-(3-methylphenyl)-5-and 6-benzoxazolyl] propyl alcohol
2-[2-(4-methylphenyl)-5-and 6-benzoxazolyl] propyl alcohol
2-[2-(4-trifluoromethylphenyl)-5-and 6-benzoxazolyl] propyl alcohol
2-[2-(4-methoxyphenyl)-5-and 6-benzoxazolyl] propyl alcohol
2-[2-(4-bromophenyl)-5-and 6-benzoxazolyl] propyl alcohol
2-[2-(4-fluorophenyl)-5-and 6-benzoxazolyl] propyl alcohol
2-[2-(2-methylphenyl)-5-and 6-benzoxazolyl] propyl alcohol
2-[2-(2-methoxyphenyl)-5-and 6-benzoxazolyl] propyl alcohol C(ii) the $C_{1-4}$ alkyl esters of the alsohols of C(i) above, Examples of the most preferred compounds of the invention are:

D(i) 2-[2'-phenyl-5- and 6-benzoxazolyl] propionic acid
2-[2-(3,4-dimethoxyphenyl)-5- and 6-benzoxazolyl] propionic acid
2-[2-(3,4-methylenedioxyphenyl)-5- and 6-benzoxazolyl] propionic acid
2-[2-(2-chlorophenyl)-5- and 6-benzoxazolyl] propionic acid
2-[2-(2-fluorophenyl)-5- and 6-benzoxazolyl] propionic acid
2-[2-(2-methylphenyl)-5- and 6-benzoxazolyl] propionic acid
2-[2-(3,4-dichlorophenyl)-5- and 6-benzoxazolyl] propionic acid
2-[2-(3,5-dichlorophenyl)-5- and 6-benzoxazoly] propionic acid
2-[2-(2,4-dichlorophenyl)-5- and 6-benzoxazolyl] propionic acid
2-[2-(3-chlorophenyl)-5- and 6-benzoxazolyl] propionic acid
2-[2-(3-trifluoromethylphenyl-5- and 6-benzoxazolyl] propionic acid
2-[2-(3-fluorophenyl)-5- and 6-benzoxazolyl] propionic acid
2-[2-(3-methylphenyl)-5- and 6-benzoxazolyl] propionic acid
2-[2-(4-iodophenyl)-5- and 6-benzoxazolyl] propionic acid
2-[2-(4-chlorophenyl)-5- and 6-benzoxazolyl] propionic acid
2-[2-(2-hydroxy-4-chlorophenyl)-5- and 6-benzoxazolyl] propionic acid
2-[2-(4-bromophenyl)-5- and 6-benzoxazolyl] propionic acid
2-[2-(4-nitrophenyl)-5- and 6-benzoxazolyl] propionic acid
2-[2-(4-fluorophenyl)-5- and 6-benzoxazolyl] propionic acid
2-[2-(3-nitro-4-chlorophenyl)-5- and 6-benzoxazolyl] propionic acid
2-[2-(4-methylphenyl)-5- and 6-benzoxazolyl] propionic acid
2-[2-(2-acetylphenyl)-5- and 6-benzoxazolyl] propionic acid
2-[2-(4-trifluoromethylphenyl)-5- and 6-benzoxazolyl] propionic acid
2-[2-(4-methoxyphenyl)-5- and 6-benzoxazolyl] propionic acid
2-[2-(4-methylsulphonylphenyl)-5- and 6-benzoxazolyl] propionic acid
2-[2-(2-methoxyphenyl)-5- and 6-benzoxazolyl] propionic acid D(ii) the sodium, potassium, aluminum and ammonium salts of the acids of D(i) above, and D(iii)the $C_{1-4}$ alkyl, amino-$C_{1-4}$ alkyl, dimethylamino-$C_{1-4}$ alkyl and diethylamino-$C_{1-4}$ alkyl esters of the acids of D(i) above.

The present invention also provides a process for preparing the foregoing compounds of formula I which comprises cyclising a compound of the formula :-

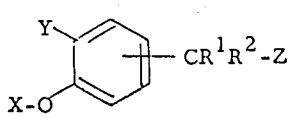

wherein Z is the group $R^3$ or is a group convertible to $R^3$, and either X is hydrogen or the group $R^{10}CO—$ and Y is $H_2N—$ or X is hydrogen and Y is the group $R^{10}CO—NH—$ or $R^{10}CH=N—$, $R^{10}$ being the same as $R^4$ with the exception of hydroxy, amino or $C_{2-7}$ acylamino, the cyclisation being carried out, in the case where X is hydrogen and Y is $H_2N—$, in the presence of a cyclising agent capable of donating the required group $R^4$ (other than $C_{2-7}$ acylamino), and thereafter, where Z in the resultant compound is not the same as group $R^3$, it is converted to group $R^3$ in conventional manner and, if desired, a resultant compound in which $R^4$ is amino is acylated to produce a compound of formula I in which $R^4$ is $C_{2-7}$ acylamino.

In carrying out the foregoing cyclisation using a compound of the formula III in which X is hydrogen and Y is $H_2N—$, it will be appreciated that, if group Z is also capable of reacting with the cyclising agent used, the reaction may produce a mixture of products rather than the desired compound of formula I alone. Although the undesired products could be separated from the reaction mixture, it is obviously desirable to use a compound of formula III in which Z is a group which is incapable of reaction with the cyclising agent. Thus, in the case where Z is a group convertible to $R^3$, Z is preferably hydrogen or halogen and where Z is one the groups encompassed by $R^3$, it is preferably a nitrile group or an esterified carboxy, esterified hydroxymethyl, carboxyamide or salified carboxy group.

The cyclisation of a compound of formula III in which X is hydrogen and Y is $R^{10}CO—NH—$ or in which X is $R^{10}CO—$ and Y is $H_2N$ may be carried out under the influence of heat and/or under acidic conditions, for example in the presence of hydrochloric acid or polyphosphoric acid. In the case where X is hydrogen and Y is $R^{10}CH=N—$, cyclisation is easily accomplished by treatment with an oxidising agent such as lead tetra-acetate or nickel peroxide.

When a compound of formula III in which X is hydrogen and Y is $H_2N—$ is used, cyclisation is normally accomplished by mixing the cyclising agent with the compound of formula III, usually in a suitable solvent which may be water or an organic solvent such as pyridine, at room teperature or below followed by the application of heat to complete the reaction. Examples of suitable cyclising agents which may be used are compounds of the formulae $R^{10}COOH$, $(R^{10}CO)_2O$, $R^{10}COCl$, $R^{10}CONH_2$, $R^{10}CONHNH_2$, $R^{10}CN$, $R^{10}C(OR')=NH$ and $R^{10}CCl=NR'$ where $R'$ is $C_{1-4}$ alkyl, or the cyclising agent may be a cyanogen halide, preferably cyanogen bromide, when $R^4=NH_2$ is required, or phosgene when $R^4=OH$ is required.

As stated above, when Z is not the group $R^3$, completion of the cyclisation step must be followed by conversion of group Z to the desired group $R^3$. As is well known in the art, many different types of groups may be converted to the $R^3$ functions in the desired compounds of this invention. However, it is preferred for the purposes of the present invention that, where Z is not the group $R^3$, it is hydrogen or halogen. When Z is hydrogen, the compound resulting from the cyclisation reaction may be halogenated in conventional manner, for example using chlorine, sulphurylchloride, bromine or N-bromosuccinimide, preferably in the presence of a suitable solvent such as carbon tetrachloride to produce the corresponding compound in which Z is halogen. This compound, or the same compound obtained directly from the above cyclisation reaction, may then be reacted with an alkali metal cyanide in a suitable diluent or solvent, usually under the influence of heat, to produce a compound of formula I in which $R^3$ is CN.

The latter compound, or the same compound obtained directly from the above cyclisation reaction, may then be treated in a number of ways to achieve its conversion to another compound of formula I. For example, the nitrile may be reacted with an appropriate alcohol under acidic conditions to produce a compound of formula I in which $R^3$ is an esterified carboxy group. Alternatively, the nitrile can be hydrolysed, for example using sulphuric acid, to produce a compound of formula I in which $R^3$ is a carboxyamide group. Hydrolysis of the nitrile, or the last mentioned carboxyamide, with a strong base or an acid such as concentrated hydrochloric acid results in the formation of a compound of formula I in which $R^3$ is a carboxy group. A resultant compound of formula I in which $R^3$ is esterified carboxy may be converted to a hydroxamic acid derivative by reaction with hydroxylamine. A resultant acid of formula I, i.e. where $R^3$ is a carboxy group or an ester thereof may readily be reduced, for example using diborane or a complex metal hydride, to yield the corresponding compound of formula I in which $R^3$ is hydroxymethyl and the alcohol resulting therefrom may then be esterified in conventional manner, for example by reaction with an appropriate carboxylic acid such as $C_{2-4}$ alkanoic acid.

An acid of formula I may be salified by treatment with an appropriate base such as ammonium, alkylammonium, aralkylammonium, aluminium, alkali metal or alkaline earth metal hydroxide and of course a salt of formula I may readily be converted to the free acid by treatment with an acid such as hydrochloric or sulphuric acid. An acid of formula I or a salt thereof may be converted to an ester by treatment with an appropriate alcohol or by treatment with a halide of the appropriate ester moiety or a salt of that halide if the ester moiety contains a basic nitrogen atom. An ester of formula I may of course be hydrolysed to the corresponding acid or alcohol of formula I by treatment with a suitable hydrolytic agent such as an inorganic base or acid. An acid of formula I or an ester thereof may also be converted to an amide of formula I by reaction with ammonia or an appropriate primary or secondary amine.

A resultant compound of formula I in which $R^1$ and/or $R^2$ is hydrogen may be alkylated to produce the corresponding compound of formula I in which $R^1$ and/or $R^2$ is $C_{1-6}$ alkyl. The alkylation may be carried out by interaction of an alkali metal derivative of the appropriate benzoxazole derivative with an alkyl halide such as, for example, methyl or ethyl iodide.

Finally, in a situation where it may prove difficult by the above route to produce a compound of formula I in which both the group $R^4$ and the group $—CR^1R^2R^3$ have the desired meanings, a compound of formula I in which group $R^4$ is not the desired group may be prepared, the oxazole ring in the resultant compound is then cleaved in such a way as to regenerate a compound of formula III in which X is hydrogen and Y is $H_2N—$, for example by cleavage with concentrated hydrochloric acid at a temperature of around 150°C., and the resultant compound of formula III is re-cyclised in the presence of a cyclising agent which will donate the required group $R^4$.

The compounds of formula III above in which Z is the group $R^3$ and X and Y are as defined above are novel compounds. Such novel compounds form a part of this invention and may be prepared by reducing the corresponding nitro compounds in the case where a compound of formula III in which $Y = H_2N-$ is required, followed by acylation of a resulting compound in which X is hydrogen and Y is $H_2N-$ or treatment of the latter compound with the aldehyde $R^{10}CHO$ to produce a compound of formula III in which Y is the group $R^{10}.CO-NH-$ or $R^{10}CH=N-$ respectively.

The following reaction scheme shows the preparation of the above mentioned nitro intermediates from known or readily prepared chemicals.

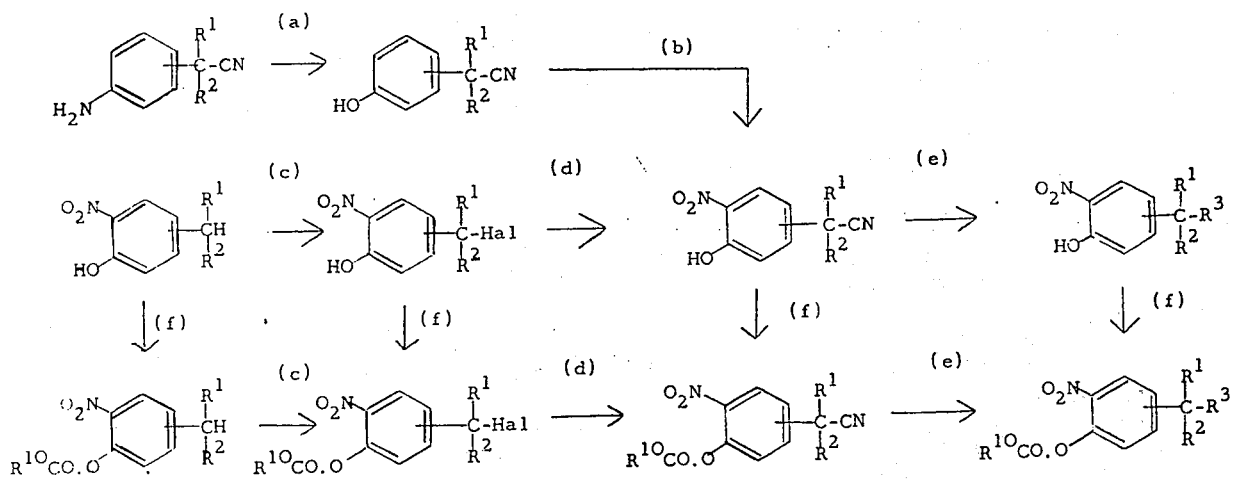

In the above scheme, step (a) is accomplished by diazotisation followed by treatment of the resultant diazonium compound with dilute sulphuric acid. Step (b) is carried out by nitration, for example by addition of nitric acid to a solution of the nitrile in glacial acetic acid. Steps (c), (d) and (e) are as described above in connection with the conversion of $Z=H \rightarrow Z=$ Halogen $\rightarrow Z=CN \rightarrow Z=R^3$. Step (f) is accomplished by conventional acylation using an appropriate acylating agent such as an acyl halide or acid anhydride.

The compounds of formula I above in which $R^3$ is a nitrile group are, as can be seen from the foregoing description, useful as intermediates for conversion to other compounds of formula I. These other compounds, i.e. where $R^3$ is carboxy or a salt, ester, amide or hydroxamic acid derivative thereof, or is hydroxymethyl or an ester thereof, are useful in that they are pharmacologically active. In particular, these compounds have been shown to have low toxicity and to possess analgesic, antipyretic and/or anti-inflammatory activity as well as possessing in certain cases the ability to inhibit prostaglandin synthesis or release.

The foregoing activities have been demonstrated in tests carried out in animals usually at doses of from 0.1 to 250 mg./kg. In the treatment of humans, the dose administered may be, for example, between 0.1 and 25 mg./kg. but, of course, doses outside this range may be used at the discretion of the physician treating the patient. The pharmacologically active compounds of formula I may be administered by the enteral or or parenteral routes and for this purpose they will normally be formulated into pharmaceutical compositions comprising the active ingredient in association with at least one pharmaceutically acceptable carrier therefor. Such compositions form a part of this invention and will normally consist of the active ingredient mixed with a carrier, or diluted by a carrier, or enclosed or encapsulated by a carrier in the form of a capsule, sachet, cachet or other container. The carrier may be a solid, semi-solid or liquid material which serves as a vehicle, excipient, coating agent, or medium for the active ingredient. Some examples of the carriers which may be used are lactose, dextrose, sucrose, sorbitol, mannitol, starch, gum acacia, calcium phosphate, liquid paraffin, cocoa butter, oil of theobroma, alginates, tragacanth, gelatin, methyl cellulose, polyoxyethylene sorbitan monolaurate, methyl - or propyl - hydroxybenzoate, ethyl cellulose acetate phthalate, low viscosity acetyl cellulose acetate, paraffin wax, mineral wax, vegetable wax, vegetable gum, silicone rubbers such as liquid polydimethylsiloxane rubber, plasticised or unplasticised polyvinyl chloride, plasticised polyethylene terephthalate, modified collagen, cross-linked hydrophilic polyether gel, cross-linked polyvinyl alcohol or cross-linked partially hydrolysed polyvinyl acetate.

Advantageously the compositions of the invention are formulated in a dosage unit form containing from 1 to 1000 mg. (preferably 25 to 500 mg.) of the active ingredient. Examples of suitable dosage unit forms are tablets, hard or soft gelatin capsules, microcapsules and suppositories as well as drug dispensing systems comprising the active ingredient contained in a flexible, imperforate polymeric material through which the drug may be released slowly by diffusion. More generally, the term "dosage unit form" as used herein means a physically discrete unit containing the active ingredient, generally in admixture with and/or enclosed by a pharmaceutical carrier, the quantity of active ingredient being such that one or more units are normally required for a single therapeutic administration.

In addition to the active ingredient of formula I, the compositions of the present invention may also contain one or more pharmacologically active ingredients, for example, acetylsalicylic acid and salts thereof, caffeine, codeine phosphate, phenylbutazone, paracetamol, dextropropoxyphene and indomethacin.

The compositions of the present invention will of course be adapted to the particular route of administration. Thus, for oral administration, tablets, pills, capsules, solutions or suspensions may be used; for parenteral administration, sterile injection solutions or suspensions may be used; for rectal administration, suppositories may be used; and for topical administration, creams, lotions or ointments may be used. Any of the foregoing compositions may, of course, be formulated in delayed or sustained release form in a manner well known in the art.

The following examples will further illustrate the preparation of the novel intermediates and novel end-products of formula I :

EXAMPLE 1

2-(2-Phenyl-5-benzoxazolyl) propionic acid (a) 2-(4-Hydroxyphenyl) propionitrile Finely ground 2-(4-aminophenyl) propionitrile (73 g., 0.5 mole) was suspended in concentrated hydrochloric acid (125 ml.). The stirred suspension was diazotised at 0°–5°C by the dropwise addition of a solution of sodium nitrite (36.23 g., 0.525 mole) in water (60 ml.) during 1–2 hours. The almost clear solution was stirred for a further 20 minutes at 5°–10°C, then poured into a stirred, boiling solution of concentrated sulphuric acid (250 ml.) in water (2.5 l.). After 6 minutes it was cooled in an ice-bath, then extracted with ether (x4). The combined ether extracts were extracted with 2N-sodium hydroxide solution (x6). The combined alkaline extracts were cooled in ice-bath, acidified with concentrated hydrochloric acid and extracted with ether (x3). The combined ether extracts were washed with saturated sodium chloride solution (x3), dried ($Na_2SO_4$) and evaporated to leave a dark brown oil (66.7 g.) which on distillation gave 2-(4-hydroxyphenyl) propionitrile (59.58 g.), b.p. 112°–122°C/0.125 m.m., m.p. 41°–46°C.

Analysis : Calculated C : 73.44, H : 6.16, N : 9.51. Found C : 73.19, H : 5.91, N : 9.31.

(b) 2-(3-Nitro-4-hydroxyphenyl) propionitrile

A solution of 2-(4-hydroxyphenyl) propionitrile (7.79 g., 0.053 mole.) in glacial acetic acid (10 ml.) was added at 7°–10°C, with stirring, to 12 N-nitric acid (8 ml.) during 45 minutes. A further volume (10 ml.) of glacial acetic acid was added during this period. The resulting yellow suspension was stirred for a further 30 minutes at 7°–10°C, then for 30 minutes at −10° to −15°C. The suspension was diluted with water (approx. 90 ml.). Filtration yielded 2-(3-nitro-4-hydroxyphenyl) propionitrile as a yellow solid (8.43 g.), m.p. 78°–81°C.

Analysis : Calculated C : 56.24, H : 4.19, N : 14.57. Found C : 56.29, H : 4.24, N : 14.47.

(c) (i) 2-(3-Amino-4-hydroxyphenyl) propionitrile 2-(3-Nitro-4-hydroxyphenyl) propionitrile (123.8 g., 0.64 mole.) was suspended in absolute ethanol (950 ml.) and added during 20 minutes, with cooling, to a solution of stannous chloride dihydrate (437.8 g., 1.94 mole.) in concentrated hydrochloric acid (591 ml., 7 mole.). The addition was made at such a rate that the temperature of the reaction mixture did not exceed 20°C. Stirring of the mixture was continued for a further 19 hours at room temperature. The resulting solution, together with ice (1.75 kg.) was added during one hour to a cooled solution of sodium hydroxide (650 g.) in water (600 ml.). The temperature of the reaction mixture was maintained at 15°–20°C during the addition. The mixture was stirred for a further 1 hour, and the pH then adjusted to 6 by the addition of concentrated hydrochloric acid. The resulting suspension was filtered and the filtrate saturated with sodium chloride, then extracted with ether (x6). The combined ether extracts were dried ($Na_2SO_4$) and evaporated to leave a solid (69.15 g.) which was suspended in chloroform and extracted with 2N-hydrochloric acid (x6). The combined acid extracts were neutralised to pH 7–8 by the addition of sodium bicarbonate. The resulting suspension was extracted with ether (x4). The combined ether extracts were washed twice with water, dried ($Na_2SO_4$), and evaporated to yield 2-(3-amino-4-hydroxyphenyl) propionitrile as a light brown solid (62.85 g.), m.p. 110°–112°C.

Analysis : Calculated C : 66.64, H : 6.21, N : 17.27. Found C : 66.45, H : 6.09, N : 16.99.

(c) (ii) 2-(3-Amino-4-hydroxyphenyl) propionitrile was also prepared by the following method:

2-(3-Nitro-4-hydroxyphenyl) propionitrile (38.4 g., 0.2 mole.) was suspended in absolute ethanol (250 ml.) and hydrogenated at 4 atmospheres pressure and room temperature over 10% palladium on charcoal. Hydrogenation was complete in 3.8 hours. The catalyst was removed by filtration. Evaporation of the filtrate yielded 2-(3-amino-4-hydroxyphenyl) propionitrile (17 g.), m.p. 110°C.

(d) 2-(3-Benzamido-4-hydroxyphenyl) propionitrile

Benzoyl chloride (27.09 g., 0.19 mole.) was added, with cooling, during 20 minutes to a stirred solution of 2-(3-amino-4-hydroxyphenyl) propionitrile (28.35 g., 0.175 mole.) in dry pyridine (200 ml.) at 0°–3°C. After addition was complete, the mixture was heated at 100°C. for 1 hour. It was then evaporated under reduced pressure to yield crude 2-(3-benzamido-4-hydroxyphenyl) propionitrile as an oil.

(e) 2-(2-Phenyl-5-benzoxazolyl) propionitrile

The oil from (d) above was boiled for 30 minutes during which time the temperature of the vapour above the oil rose to 130°C. On cooling the residue solidified. Recrystallisation of the solid from methanol yielded 2-(2-phenyl-5-benzoxazolyl) propionitrile (27.65 g.), m.p. 118°–120°C.

Analysis : Calculated C : 77.39, H : 4.87, N : 11.28. Found C : 77.33, H : 5.11, N : 11.34.

(f) 2-(2-Phenyl-5-benzoxazolyl) propionic acid

A solution of 2-(2-phenyl-5-benzoxazolyl) propionitrile (24 g., 0.096 mole.) in concentrated hydrochloric acid (220 ml.) was refluxed for 2.5 hours. The mixture was poured into ice/water (1 liter). The precipitated 2-(2-phenyl-5-benzoxazolyl) propionic acid was filtered off and washed well with water. The dry acid weighed 23 g. and had m.p. 177°–179°C.

Analysis : Calculated C : 71.89, H : 4.90, N : 5.24. Found C : 72.13, H : 4.95, N : 5.39.

EXAMPLE 2

In a similar manner to that of Example 1, the following compounds were synthesised :

(a) 2-(2-p-Fluorophenyl-5-benzoxazolyl) propionic acid, m.p. 162° – 164°C.

Analysis : Calculated C : 67.36, H : 4.24, N : 4.91. Found C : 67.58, H : 4.45, N : 5.07.

(b) 2-(2-p-Chlorophenyl-5-benzoxazolyl) propionic acid, m.p. 188°–191°C.

Analysis : Calculated C : 63.68, H : 4.00, N : 4.64. Found C : 63.50, H : 4.16, N : 4.72.

(c) 2-(2-m-Chlorophenyl-5-benzoxazolyl) propionic acid, m.p. 173°–175°C

Analysis : Calculated C : 63.68, H : 4.00, N : 4.64. Found C : 63.50, H : 4.01, N : 4.75.

(d) 2-(2-p-Methylphenyl-5-benzoxazolyl) propionic acid, m.p. 166°–168°C.

Analysis : Calculated C : 72.58, H : 5.37, N : 4.97. Found C : 72.36, H : 5.46, N : 5.4.

(e) 2-(2-m-Methylphenyl-5-benzoxazolyl) propionic acid, m.p. 155°–157°C.

Analysis : Calculated C : 72.58, H : 5.37, N : 4.97. Found C : 72.39, H : 5.61, N : 5.14.

(f) 2-(2-o-Methylphenyl-5-benzoxazolyl) propionic acid, m.p. 107°–110°C.

Analysis : Calculated C : 72.58, H : 5.37, N : 4.97. Found C : 72.54, H : 5.59, N : 4.77.

(g) 2-(2-p-Methoxyphenyl-5-benzoxazolyl) propionic acid, m.p. 189°–191°C.

Analysis : Calculated C : 68.67, H : 5.08, N : 4.71. Found C : 68.42, H : 5.36, N : 4.72.

(h) 2-(2-o-Hydroxy-p-chlorophenyl-5-benzoxazolyl)-propionitrile, m.p. 143°–145°C. (with prior softening).

Analysis : Calculated C : 64.3, H : 3.7, N : 9.4. Found C : 64.1, H : 3.5, N : 9.5.

(i) 2-(2-o-Hydroxy-p-chlorophenyl-5-benzoxazolyl)-propionic acid, m.p. 197°–200°C.

Analysis : Calculated C : 60.5, H : 3.8, N : 4.4. Found C : 60.65, H : 4.06, N : 4.5.

(j) 2-(2-p-Chlorophenyl-5-benzoxazolyl)propionitrile, m.p. 150°–153°C.

Analysis : Calculated C : 67.96, H : 3.92, N : 9.90. Found C : 67.57, H : 3.96, N : 9.25.

(k) 2-(2-p-Acetylphenyl-5-benzoxazolyl)propionic acid, m.p. 207°–209°C.

Analysis : Calculated C : 69.90, H : 4.85, N : 4.53. Found C : 69.72, H : 4.75, N : 4.50.

EXAMPLE 3

(a) 2-(2-p-Bromophenyl-5-benzoxazolyl propionic acid, one third hydrochloride.

This compound was prepared using the procedure described in Example 1. The product, m.p. 195°–197°C, contained one third of a molecule of hydrogen chloride.

Analysis : Calculated C : 53.60, H : 3.46, N : 3.90. Found C : 53.25, H : 3.37, N : 3.88.

(b) 2-(2-p-Bromophenyl-5-benzoxazolyl) propionic acid, sodium salt.

2-(2-p-Bromophenyl-5-benzoxazolyl) propionic acid, one third hydrochloride (4.3 g., 0.012 mole.) was ground in 1N-sodium hydroxide solution(20 ml.). To the suspension was added an equal volume of chloroform. The suspension was stirred, then filtered. Recrystallisation of the solid from aqueous ethanol yielded 2-(2-p-bromophenyl-5-benzoxazolyl) propionic acid, sodium salt, m.p. >316°C.

Analysis : Calculated C : 52.19, H : 3.01, N : 3.8. Found C : 51.99, H : 3.17, N : 4.07.

EXAMPLE 4

Ethyl 2-(2-phenyl-5-benzoxazolyl) propionate 2-(2-Phenyl-5-benzoxazolyl) propionic acid (10 g., 0.037 mole.) and toluene p-sulphonic acid (0.5 g.) were dissolved in a mixture of benzene (60 ml.) and absolute ethanol (25 ml.). The solution was refluxed for 12 hours. After cooling the solution was washed twice with 2N-sodium hydroxide solution, then several times with water. After drying ($Na_2SO_4$) it was evaporated under reduced pressure to leave ethyl 2-(2-phenyl-5-benzoxazolyl) propionate (8 g.) as an oil, which solidified on cooling, m.p. 45°–46°C.

Analysis : Calculated C : 73.20, H : 5.80, N : 4.74. Found C : 72.95, H : 5.51, N : 4.79.

In a similar manner, the following compound was prepared:

Ethyl 2-(2-p-chlorophenyl-5-benzoxazolyl)propionate, m.p. 59°–62°C.

Analysis : Calculated C : 65.54, H : 4.89, N : 4.24. Found C : 65.46, H : 4.85, N : 4.11.

EXAMPLE 5

2-(2-Phenyl-5-benzoxazolyl) propyl alcohol

An approximately 1M-solution (15 ml.) of diborane in dry tetrahydrofuran was added during 5 minutes to a stirred suspension of 2-(2-phenyl-5-benzoxazolyl) propionic acid (3 g., 0.011 mole.) in dry tetrahydrofuran (10 ml.) at room temperature. The resulting solution was stirred for 3.75 hours at room temperature, then poured onto crushed ice (35 g.) containing concentrated hydrochloric acid (75 ml.). The mixture was extracted with chloroform (x2). The combined chloroform extracts were washed twice with a saturated sodium bicarbonate solution, dried ($Na_2SO_4$), and evaporated under reduced pressure to give hydrated 2-(2-phenyl-5-benzoxazolyl) propyl alcohol (2.56 g.) as a solid, m.p. 99°–103°C.

Analysis : Calculated (for $C_{16}H_{15}NO_2.¼H_2O$): C : 74.53, H : 6.05, N : 5.43. Found C : 74.74, H : 5.95, N : 5.41.

EXAMPLE 6

2-(2-Amino-5-benzoxazolyl) propionic acid (a) 2-(3-Amino-4-hydroxyphenyl) propionic acid A suspension of 2-(3-amino-4-hydroxyphenyl) propionitrile (10 g., 0.06 mole) in concentrated hydrochloric acid (100 ml.) was refluxed for 2.25 hours. The resulting solution was cooled and the pH adjusted to 5 by the addition of 2N-sodium hydroxide solution. The precipitated solid was filtered off. Recrystallisation of the solid from methanol yielded 2-(3-amino-4-hydroxyphenyl) propionic acid (6g.), m.p. 167°–169°C.

Analysis : Calculated C : 59.65, H : 6.12, N : 7.73. Found C : 59.43 H : 6.13, N : 7.94.

(b) 2-(2-Amino-5-benzoxazolyl) propionic acid

Cyanogen bromide (1.06 g., 0.1 mole.) was added to a stirred suspension of 2-(3-amino-4-hydroxyphenyl) propionic acid (1.8 g., 0.1 mole.) in water (100 ml.). The suspension was stirred at room temperature for a further 41 hours. The pH of the suspension was adjusted to 4 by the addition of 50% w/v sodium hydroxide solution. The suspension was filtered and the solid was washed (x2) with small volumes of water. Recrystallisation of the solid from 50% aqueous methanol gave 2-(2-amino-5-benzoxazolyl) propionic acid (1.46 g.), m.p. 225°–229°C.

Analysis : Calculated C : 58.24, H : 4.88, N : 13.58.
Found C : 58.50, H : 4.85, N : 13.46.

EXAMPLE 7

2-(5-Benzoxazolyl) propionic acid (a) Ethyl 2-(3-amino-4-hydroxyphenyl) propionate A solution of 2-(3-amino-4-hydroxyphenyl) propionic acid (13.82 g., 0.076 mole.) in absolute ethanol (50 ml.) was saturated with dry hydrogen chloride. The solution was refluxed for 5.5 hours. During the first 1.75 hours of reflux, hydrogen chloride was admitted to the solution. The solution was evaporated under reduced pressure to leave an oil. The oil was dissolved in water (50 ml.) and the pH of the solution adjusted to 8 by the addition of sodium bicarbonate. The solution was extracted with ether (x3). The combined ether extracts were dried ($Na_2SO_4$) and evaporated to leave an oil. Distillation of the oil yielded ethyl 2-(3-amino-4-hydroxyphenyl) propionate (8.43 g.), b.p. 154°–156°C/0.25 m.m., m.p. 79°–82°C.

Analysis : Calculated C : 63.13, H : 7.22, N: 6.69.
Found C : 62.48, H : 7.24, N : 6.79.

(b) Ethyl 2-(3-formamido-4-hydroxyphenyl) propionate

A solution of ethyl 2-(3-amino-4-hydroxyphenyl) propionate (2 g., 0.01 mole.) in 98% formic acid (10 ml.) was refluxed for 1.5 hours. The solution was evaporated under reduced pressure to leave an oil. The oil was stirred in ether (10 ml.). Filtration yielded ethyl 2-(3-formamido-4-hydroxyphenyl) propionate as a white solid (0.8 g.), m.p. 102°–104°C.

(c) Ethyl 2-(5-benzoxazolyl) propionate

Ethyl 2-(3-formamido-4-hydroxyphenyl) propionate (11.39 g., 0.048 mole.) was heated at 250° ± 5°C in an oil-bath for 20 minutes. After cooling the oil was dissolved in ethyl acetate. The solution was washed with 2N-sodium hydroxide solution (x4), then with water (x2). The solution was dried ($Na_2SO_4$) and evaporated to give ethyl 2-(5-benzoxazolyl) propionate as an oil (6.55 g.).

(d) 2-(5-Benzoxazolyl) propionic acid

A suspension of ethyl 2-(5-benzoxazolyl) propionate (5.75 g., 0.026 mole.) in a solution of sodium hydroxide (1.04 g., 0.026 mole.) in water (150 ml.) was stirred at room temperature for 4.4 hours. The resulting turbid solution was clarified by washing with ethyl acetate (x3) before adjusting the pH to 4 by the addition of concentrated hydrochloric acid. The ensuing turbid solution was saturated with sodium chloride, then extracted with ethyl acetate (x3). The combined ethyl acetate extracts were washed once with saturated aqueous sodium chloride solution, dried ($Na_2CO_4$) and evaporated to leave a solid. The solid was stirred in boiling carbon tetrachloride (150 ml.) and the hot suspension was filtered. The filtrate was evaporated to give 2-(5-benzoxazolyl) propionic acid as a solid (1.24 g.), m.p. 126°–128.5°C.

EXAMPLE 8

2-Phenyl-5-benzoxazolyl acetic acid

A solution of 2-phenyl-5-benzoxazolylacetonitrile (8.9 gm.) — prepared by the method described in Example 1(e) — in concentrated hydrochloric acid (80 ml.) was heated on a steam bath for 2.5 hours. The solution was then diluted with ice/water and allowed to stand. The solid produced was crystallised from toluene to give white crystals of 2-phenyl-5-benzoxazolyl acetic acid, m.p. 175°C.

Analysis : Calculated (for $C_{15}H_{11}NO_3$): C : 71.1, H : 4.4, N : 5.5.
Found C : 71.0, H : 4.4, N : 5.6.

EXAMPLE 9

2-Phenyl-6-benzoxazolyl acetic acid (a) 6-Methyl-2-phenylbenzoxazole

Benzoyl chloride (79 ml) was slowly added to a stirred suspension of 6-amino-m-cresol(83 gm) in pyridine (600 ml). The temperature was kept below 5°C. The solution was heated under reflux for 2 hr., then was evaporated to dryness to give an oil. This oil was extracted with aqueous 2N sodium hydroxide solution. The aqueous layer was made acid with concentrated hydrochloric acid. The solid, N-(2'-hydroxy-4'-methylbenzanilide), m.p. 170°C, was filtered off. This product was heated until no more water was evolved. The resulting liquid was allowed to cool and the solid produced was powdered and taken up in petroleum ether. The solution was treated with carbon and the filtrate evaporated to dryness to yield 6-methyl-2-phenyl-benzoxazole, m.p. 93°C.

(b) 6-Bromomethyl-2-phenylbenzoxazole

N-Bromosuccinimide (25.9 gm) was added to a cold solution of 6-methyl-2-phenylbenzoxazole (30 gm) in carbon tetrachloride (250 ml). Benzoyl peroxide (500 mg) was added and the mixture was heated under reflux for 3 hr. in the presence of u.v. light. The solid residue was filtered off. The filtrate was evaporated down slightly, treated with carbon and allowed to cool. The crystals which were formed were recrystallised from benzene to yield 6-bromomethyl-2-phenylbenzoxazole, m.p. 162°C.

(c) 2-Phenyl-6-benzoxazolylacetonitrile

A mixture of 6-bromomethyl-2-phenylbenzoxazole (40 gm) and sodium cyanide (7.4 gm) in dry dimethylformamide (800 ml) was heated on a steam bath for 3 hr. The mixture was filtered and the filtrate was evaporated to dryness. The solid was recrystallised to give 2-phenyl-6-benzoxazolylacetonitrile as white crystals, m.p. 144°C.

(d) 2-Phenyl-6-benzoxazolylacetic acid

A solution of 2-phenyl-6-benzoxazolylacetonitrile (11 gm) in conc. hydrochloric acid (100 ml) was heated on a steam bath for 1 hr. The solution was then allowed to cool. The resultant solid was filtered off and equilibrated between aqueous sodium bicarbonate solution and chloroform. The aqueous layer was made acid with hydrochloric acid and was extracted with chloroform. The chloroform solution was evaporated to dryness. The residue was recrystallised from toluene to give white crystals of 2-phenyl-6-benzoxazolylacetic acid, m.p. 170°C.

Analysis found: C : 71.0, H : 4.4, N : 5.5%.
$C_{15}H_{11}NO_3$ requires: C : 71.1, H : 4.4, N : 5.4%.

EXAMPLE 10

Ethyl 2-phenyl-6-benzoxazolylacetate

A solution of 2-phenyl-6-benzoxazolylacetic acid (20 gm) in ethanol (200 ml) was heated under reflux for 6 hr., during which time dry hydrogen chloride gas was passed through the solution. The residual oil on evaporation of the solution was extracted with ether and this solution was evaporated to dryness. The solid formed was recrystallised from toluene/petroleum ether to yield white crystals of ethyl-2-phenyl-6-benzoxazolylacetate, m.p. 76°C.

Analysis found: C : 72.3, H : 5.4, N : 4.8. $C_{17}H_{15}NO_3$ requires: C : 72.6, H : 5.4, N : 5.0.

EXAMPLE 11

Ethyl 2-(2-Phenyl-6-benzoxazolyl)propionate

A solution of ethyl 2-phenyl-6-benzoxazolyl acetate (34 gm) in ether (200 ml) was added to a stirred solution of $NaNH_2$ (from 3.2 gm sodium) in liquid ammonia (500 ml). This red mixture was stirred for 15 min., then a solution of methyl iodide (8.5 ml) in ether (10 ml) was added rapidly. When the reaction mixture appeared colourless the reaction was stopped by the addition of excess ammonium chloride. The mixture was evaporated to dryness and the residue was extracted with ether. The ethereal solution was evaporated to dryness to yield white crystals of ethyl 2-(2-phenyl-6-benzoxazolyl)propionate, m.p. 46°C.

Analysis found: C : 73.0, H : 5.7, N : 5.0. $C_{18}H_{17}NO_3$ requires: C : 73.2, H : 5.8, N : 4.7.

EXAMPLE 12

2-(2-Phenyl-6-benzoxazolyl) propanol

A solution of lithium aluminium hydride (~ 2 gm) in ether (50 ml) was slowly added to a solution of ethyl 2-(2-phenyl-6-benzoxazolyl)-propionate (5 g) in ether (40 ml). The mixture was heated under reflux for 1 hr., then ethyl acetate was slowly added until effervescence ceased. 6-N-Aqueous hydrochloric acid was then added and the ether layer was separated off and dried. Chromatography over silica gel yield pure 2-(2-phenyl-6-benzoxazolyl)-propanol, m.p. 98°C.

Analysis found: C : 76.0, H : 5.8, N : 5.6. $C_{16}H_{15}NO_2$ requires: C : 75.9, H : 6.0, N : 5.5.

EXAMPLE 13

2-(2-Phenyl-6-benzoxazolyl) propionamide

A mixture of ethyl 2-(2-phenyl-6-benzoxazolyl) propionate (4.4 g) and ammoniacal glycerol (40 ml) was heated at 150°C in a bomb for 18 hr. The mixture was diluted twofold with water, the resultant white solid filtered off and recrystallised from ethyl acetate to give white crystals of 2-(2-phenyl-6-benzoxazolyl) propionamide, m.p. 193°C.

Analysis found: C : 72.1, H : 5.4, N : 10.7. $C_{16}H_{14}N_2O_2$ requires: C : 72.2, H : 5.3, N : 10.5.

By the same method, the following compounds were prepared:
(a) 2-(2-Phenyl-5-benzoxazolyl)propionamide, m.p. 202°–204°C.

Analysis: Calculated C: 72.2, H: 5.3, N: 10.5. Found C: 72.0, H: 5.1, N: 10.4.
(b) 2-(2-p-Chlorophenyl-5-benzoxazolyl)propionamide, m.p. 245°–246°C.

Analysis: Calculated C: 63.89, H: 4.35, N: 9.31. Found C: 63.64, H: 4.30, N: 9.22.

EXAMPLE 14

2-(2-Phenyl-6-benzoxazolyl) propionic acid

A solution of ethyl 2-(2-phenyl-6-benzoxazolyl) propionate (15 g) in concentrated hydrochloric acid (150 ml) was heated on a steam bath for 6 hr. The solution was cooled and the crystals which formed were filtered off. These were recrystallised from ethanol/water to yield 2-(2-phenyl-6-benzoxazolyl) propionic acid, m.p. 132°C.

Analysis found: C : 71.7, H : 5.0, N : 5.3. $C_{16}H_{13}NO_3$ requires: C : 71.9, H : 4.9, N : 5.2%.

EXAMPLE 15

2-(2-p-Chlorophenyl-6-benzoxazolyl) propionic acid (a) 2-(3-Hydroxy-4-aminophenyl) propionic acid hydrochloride A solution of ethyl 2-(2-phenyl-6-benzoxazolyl) propionate (10 g) in concentrated hydrochloric acid (150 ml) was heated at 160°C for 24 hr. The resulting mixture was evaporated to dryness and the residue was taken up in water. This solution was washed with chloroform then was evaporated to dryness to yield 2-(3-hydroxy-4-aminophenyl) propionic acid hydrochloride as a white powder, m.p. 170°C (dec.).

(b) Ethyl 2-(3-hydroxy-4-aminophenyl) propionate

A solution of 2-(3-hydroxy-4-aminophenyl) propionic acid hydrochloride (5 g) in ethanol (100 ml) was saturated with hydrogen chloride and the resulting solution was heated under reflux for 6 hr. The solution was evaporated to dryness and the residue was taken up in ethanol and this solution was neutralised with sodium hydroxide solution. The residue on evaporation was taken up in chloroform and the solution was washed with water. Evaporation of the chloroform solution yielded ethyl 2-(3-hydroxy-4-aminophenyl) propionate, m.p. 114–5°C.

Analysis found: C : 63.2, H : 7.2, N : 6.9. $C_{11}H_{15}NO_3$ requires: C : 63.1, H : 7.2, N : 6.7.

(c) Ethyl 2-(2-p-chlorophenyl-6-benzoxazolyl) propionate

A solution of ethyl (3-hydroxy-4-aminophenyl) propionate (2.5 g) in pyridine (15 ml) was treated with p-chlorobenzoyl chloride (1.65 ml) at 5°C. After stirring for 2 hr. at room temperature the solution was evaporated to dryness.

The residue was heated at 220°C until no more water was evolved, then was allowed to cool. This yielded ethyl 2-(2-p-chlorophenyl-6-benzoxazolyl) propionate.

(d) 2-(2-p-Chlorophenyl-6-benzoxazolyl) propionic acid

A solution of ethyl 2-(2-p-chlorophenyl-6-benzoxazolyl) propionate (4 g) in aqueous sodium hydroxide (30 ml) was heated on a steam bath for one-half hr. On cooling the black solution was washed with chloroform. On acidification of the black solution with hydrochloric acid the mixture was extracted with chloroform. This solution on evaporation yielded 2-(2-p-chlorophenyl-6-benzoxazolyl) propionic acid, m.p. 196°C.

Analysis found: C: 63.9, H: 4.2, N: 4.8, Cl: 12.0. $C_{16}H_{12}ClNO_3$ requires: C: 63.7, H: 4.0, N: 4.6, Cl: 11.8.

In a similar manner, the following compounds were prepared:
(a) Ethyl 2-[2-(3,4-methylenedioxyphenyl)-5-benzoxazolyl]propionate, m.p. 76°–79°C.

Analysis: Calculated C: 67.25, H: 5.0, N: 4.1. Found C: 67.1, H: 5.05, N: 4.4.
(b) 2-[2-(3,4-Methylenedioxyphenyl)-5-benzoxazolyl]propionic acid, m.p. 185°–188°C.

Analysis: Calculated C: 65.5, H: 4.2, N: 4.5. Found C: 65.4, H: 3.9, N: 4.7.
(c) 2-[2-(3,4-Dichlorophenyl)-5-benzoxazolyl]propionic acid, m.p. 169°–173°C.

Analysis: Calculated C: 57.1, H: 3.3, N: 4.2. Found C: 56.9, H: 3.4, N: 4.1.

(d) 2-[2-(2,4-Dichlorophenyl)-5-benzoxazolyl]propionic acid, m.p. 151°–153°C.

Analysis: Calculated C: 57.1, H: 3.3, N: 4.2. Found C: 57.1, H: 3.3, N: 4.4.

(e) Ethyl 2-(2-p-methylsulphonylphenyl-5-benzoxazolyl)propionate, m.p. 141°–142°C.

Analysis: Calculated C: 61.1, H: 5.1, N: 3.75. Found C: 61.2, H: 5.1, N: 3.6.

(f) 2-[2-(2-Furyl)-5-benzoxazolyl]propionic acid, m.p. 160°–162°C.

Analysis: Calculated C: 65.4, H: 4.3, N: 5.4. Found C: 65.3, H: 4.4, N: 5.4.

(g) 2-(2-Cyclohexyl-5-benzoxazolyl)propionic acid, m.p. 115°–117°C.

Analysis: Calculated C: 70.30, H: 7.00, N: 5.12. Found C: 70.58, H: 6.86, N: 5.35.

(h) 2-(2-m-Trifluoromethylphenyl-5-benzoxazolyl)propionic acid, m.p. 144°–147°C.

Analysis: Calculated C: 60.89, H: 3,60, N: 4.17. Found C: 61.05, H: 3.87, N: 4.41.

(i) 2-[2-(2-Thienyl)-5-benzoxazolyl]propionic acid, m.p. 161°–163°C.

Analysis: Calculated C: 61.52, H: 4.50, N: 5.12. Found C: 61.72, H: 4.19, N: 5.07.

(j) 2-(2-o-Chlorophenyl-5-benzoxazolyl)propionic acid, m.p. 101°–103°C.

Analysis: Calculated C: 63.68, H: 4.01, N: 4.64. Found C: 63.80, H: 4.22, N: 4.82.

(k) 2-(2-p-Trifluoromethylphenyl-5-benzoxazolyl)propionic acid, m.p. 165°–168°C.

Analysis: Calculated C: 60.89, H: 3.60, N: 4.17. Found C: 60.76, H: 3.88, N: 4.34.

(l) 2-(2-p-Iodophenyl-5-benzoxazolyl)propionic acid, m.p. 205°–208°C.

Analysis: Calculated C: 48.87, H: 3.07, I: 32.27, N: 3.56. Found C: 48.91, H: 2.93, I: 32,51, N: 3.26.

(m) 2-(2-m-Fluorophenyl-5-benzoxazolyl)propionic acid, m.p. 135°–141°C.

Analysis: Calculated C: 67.36, H: 4.24, N: 4.91. Found C: 67.46, H: 4.37, N: 5.11.

(n) 2-[2-(3,5-Dichlorophenyl)-5-benzoxazolyl]propionic acid, m.p. 161°–165°C.

Analysis: Calculated C: 57.16, H: 3.29, N: 4.16. Found C: 57.13, H: 3.51, N: 4.22.

(o) 2-(2-o-Fluorophenyl-5-benzoxazolyl)propionic acid, m.p. 180°–183°C.

Analysis: Calculated C: 67.36, H: 4.24, N: 4.91. Found C: 67.16, H: 4.50, N: 4.91.

(p) 2-(2-p-Fluorophenyl-6-benzoxazolyl)propionic acid, m.p. 147°C.

Analysis: Calculated C: 67.4, H: 4.2, N: 4.9, F: 6.7. Found C: 67.2, H: 4.4, N: 4.9, F: 6.8.

(q) 2-(2-p-Chlorophenyl-5-benzoxazolyl)propionic acid, m.p. 188°–191°C.

Analysis: Calculated C: 63.68, H: 4.00, N: 4.64. Found C: 63.50, H: 4.16, N: 4.72.

EXAMPLE 16

2-(2-o-Chlorophenyl-6-benzoxazolyl)propionic acid (a) Ethyl 2-(2-o-chlorophenyl-6-benzoxazolyl)propionate A solution of o-chlorobenzaldehyde (4.3 g.) and ethyl 2-(3-hydroxy-4-aminophenyl)propionate (6 g.) in toluene (100 ml.) was heated, using a Dean and Stark apparatus to collect the water formed. After 30 minutes the solution was evaporated to dryness.

The residue was dissolved in acetic acid (100 ml.), lead tetracetate (15 g.) was added and the solution was heated on a steam bath for 1 hour. The solution was poured into ice/water and extracted with ether to give the oil, ethyl 2-(2-o-chlorophenyl-6-benzoxazolyl)propionate, a sample of which gave a satisfactory microanalysis.

(b) 2-(2-o-Chlorophenyl-6-benzoxazolyl)propionic acid

The ethyl 2-(2-o-chlorophenyl-6-benzoxazolyl)propionate from (a) was stirred with sodium hydroxide solution (50 ml.). After 1½ hours the solution was evaporated to dryness. Acidification and re-crystallisation from ether gave 2-(2-o-chlorophenyl-6-benzoxazolyl)propionic acid, m.p. 108°–110°C.

Analysis found: C: 63.5, H: 4.1, N: 4.8, Cl: 12.0. $C_{16}H_{12}ClNO_3$ requires: C: 63.7, H: 4.0, N: 4.6, Cl: 11.8.

EXAMPLE 17

2-[2-(3-Pyridyl)-5-benzoxazolyl]propionic acid

Sodium (0.115 g.) was dissolved carefully in methanol (45 ml.) and 3-cyanopyridine (5.2 g.) was added. Next day, acetic acid (0.3 g.) was added followed by 2-(3-amino-4-hydroxyphenyl)propionic acid (9.05 g.). The stirred mixture was heated under reflux for 5 hours. The solid dissolved completely during this time. An equal volume of water was added to the hot solution. On cooling, cream crystals separated which were filtered off and re-crystallised from dimethylformamide-ethanol to yield the desired acid, m.p. 197°–200°C.

Analysis: Calculated C: 67.2, H: 4.5, N: 10.4. Found C: 67.3, H: 4.3, N: 10.3.

In the same way, the following compounds were prepared:

(a) 2-[2-(4-Pyridyl)-5-benzoxazolyl]propionic acid, m.p. 247°–250°C.

Analysis: Calculated C: 67.2, H: 4.5, N: 10.4. Found C: 66.9, H: 4.8, N: 10.2.

(b) 2-[2-(2-Pyridyl)-5-benzoxazolyl]propionic acid, m.p. 177°–179°C.

Analysis: Calculated C: 67.2, H: 4.5, N: 10.4. Found C: 67.0, H: 4.5, N: 10.2.

(c) 2-(2-p-Chlorophenyl-5-benzoxazolyl)propionic acid, m.p. 188°C.

Analysis: Calculated C: 63.68, H: 4.00, N: 4.64. Found C: 63.50, H: 4.16, N: 4.72.

EXAMPLE 18

N,N-Diethyl 2-(2-phenyl-5-benzoxazolyl)propionamide 2-(2-Phenyl-5-benzoxazolyl)propionic acid (50 g.) and thionyl chloride (20 ml.) were heated together on a steam bath for 20 minutes. The excess of thionyl chloride was removed by evaporation under reduced pressure. The residue was cooled to 0°C. and treated cautiously with an excess of diethylamine. After 1 hour the reaction mixture was equilibrated between water (100 ml.) and ether (100 ml.). The ether layer was washed three times with water (50 ml.), dried ($Na_2SO_4$), and evaporated. The residue was chromatographed on silica gel and then re-crystallized from a small volume of ethanol to yield the required diethylamide, m.p. 108°–110°C.

Analysis: Calculated C: 74.5, H: 6.8, N: 8.7. Found C: 74.6, H: 6.6, N: 8.7.

EXAMPLE 19

2-(2-Phenyl-5-benzoxazolyl)propionylhydroxamic acid

A solution of sodium (0.16 g.) in absolute ethanol (5 ml.) was added to a solution of hydroxylamine hydrochloride (0.46 g.) in absolute ethanol (12 ml.). The chilled mixture was filtered and a solution of ethyl 2-(2-phenyl-5-benzoxazolyl)propionate (2.0 g.) in ethanol (10 ml.) was added to the filtrate. On standing at room temperature for 3 days, a precipitate formed which was filtered off. The solid was stirred in aqueous acetic acid and filtered off, dried, and re-crystallised from dimethylformamide-ethanol. The resulting white crystals of the desired hydroxamic acid melted at 204°–205°C.

Analysis: Calculated C: 68.1, H: 5.0, N: 9.9. Found: C: 68.1, H: 5.0, N: 9.75.

EXAMPLE 20

2-(p-Chlorophenyl)-5-benzoxazolylacetic acid

A suspension of p-chlorobenzimidoethyl ether hydrochloride (16.5 g.) and 3-amino-4-hydroxyphenylacetic acid (12.53 g.) in methanol (75 ml.) was refluxed for 2 hours. After standing at room temperature overnight the white solid product was removed by filtration. Re-crystallisation from ethanol gave the required acid, m.p. 241°–242°C.

Analysis: Calculated C: 62.61, H: 3.50, N: 4.86. Found C: 62.89, H: 3.59, N: 4.92.

EXAMPLE 21

2-(2-p-Chlorophenyl-5-benzoxazolyl)propionic acid, sodium salt, monohydrate

Sodium dicarbonate (1.95 g.) was added to a solution of 2-(2-p-chlorophenyl-5-benzoxazolyl)propionic acid (7 g.) in a mixture of methanol (100 ml.), chloroform (50 ml.) and water (60 ml.). The resulting solution was evaporated to leave a white solid. The solid was washed with chloroform (100 ml.), filtered off and dried to yield the desired sodium salt, monohydrate, m.p. 312°–314°C.

Analysis: Calculated C: 56.23, H: 3.83, N: 4.09. Found C: 56.65, H: 3.50, N: 3.99.

EXAMPLE 22

2-(2-Methyl-5-benzoxazolyl)propionic acid (a) Ethyl 2-(3-acetamido-4-hydroxyphenyl)propionate A solution of ethyl 2-(3-amino-4-hydroxyphenyl)propionate (10.46 g.) and acetic anhydride (5.6 g.) in dry pyridine (50 ml.) was heated on a steam bath for 1.25 hours. The reaction mixture was poured into water (500 ml.), precipitating an oil. On cooling the oil solidified. The solid was removed by filtration and washed with water. After drying, ethyl 2-(3-acetamido-4-hydroxyphenyl)propionate (8.25 g.) was obtained, m.p. 137°–141°C.

Analysis: Calculated C: 62.13, H: 6.82, N: 5.57. Found C: 61.96, H: 6.63, N: 5.81.

(b) Ethyl 2-(2-methyl-5-benzoxazolyl)propionate

This compound was prepared by the method described in Example 7(c) from ethyl 2-(3-acetamido-4-hydroxyphenyl)propionate.

(c) 2-(2-Methyl-5-benzoxazolyl)propionic acid

This compound was prepared from ethyl 2-(2-methyl-5-benzoxazolyl)propionate using the method of Example 7(d), m.p. 115°–117°C.

Analysis: Calculated C: 64.37, H: 5.40, N: 6.82. Found C: 64.15, H: 5.43, N: 6.85.

EXAMPLE 23

2-(2-Phenyl-5-benzoxazolyl)isobutyric acid

By treatment of 2-(2-phenyl-5-benzoxazolyl)propionitrile with methyl iodide in the manner described in Example 12, there was obtained 2-(2-phenyl-5-benzoxazolyl)isobutyronitrile which, on treatment with concentrated hydrochloric acid as described in Example 1(f), yielded 2-(2-phenyl-5-benzoxazolylisobutyric acid, m.p. 92°–95°C.

Analysis: Calculated C: 77.9, H: 5.3, N: 10.7. Found C: 77.6, H: 5.3, N: 10.45.

EXAMPLE 24

2-[2-(3-Nitro-4-chlorophenyl)benzoxazol-5-yl]propionic acid

A solution of 3-nitro-4-chlorobenzaldehyde (0.925 g.) and 2-(3-amino-4-hydroxyphenyl)propionic acid (0.900 g.) in ethanol (25 ml.) was heated under reflux for 3.5 hours. The solution was evaporated to give a solid Schiff's base which was dissolved in hot acetic acid (50 ml.). Lead tetracetate (2.8 g.) was added and the reaction was allowed to cool to room temperature. Next morning, water (200 ml.) was added which resulted in the deposition of a sticky solid. The latter was dried and triturated with a small amount of chloroform to yield the pure benzoxazole acid (0.5 g.), m.p. 210°–213°C.

Analysis: Calculated C: 55.4, H: 3.2, N: 8.1. Found C: 55.2, H: 3.2, N: 8.05.

In a similar manner, the following compound was prepared: 2-(2-p-Nitrophenyl-5-benzoxazolyl)propionic acid, m.p. 211°–217°C.

Analysis: Calculated C: 61.53, H: 3.87, N: 8.97. Found C: 61.29, H: 3.75, N: 8.68.

EXAMPLE 25

2-(2-Hydroxy-5-benzoxazolyl)propionic acid

Phosgene was bubbled through a stirred solution of 2-(3-amino-4-hydroxyphenyl)propionic acid (3.14 g.) in water (30 ml.) and concentrated hydrochloric acid (2 ml.) for 2 hours. During this time, a small amount of tar was deposited. The aqueous solution was decanted and kept at room temperature for 3 days. A solid was precipitated which was filtered off and re-crystallised from 50% aqueous isopropanol to yield the desired hydroxy compound as crystals, m.p. 174°–176°C.

Analysis: Calculated C: 57.96, H: 4.37, N: 6.76. Found C: 58.12, H: 4.36, N: 6.66.

EXAMPLE 26

2-Phenyl-6-benzoxazolyl ethanol

Ethyl 2-phenyl-6-benzoxazolylacetate, treated with lithium aluminium hydride in the manner described in Example 13, yielded 2-phenyl-6-benzoxazolyl ethanol, m.p. 89°C.

Analysis found: C: 75.5, H: 5.6, N: 5.8. $C_{15}H_{13}NO_2$ requires: C: 75.3, H: 5.5, N: 5.9.

EXAMPLE 27

In a manner similar to that of Example 6(a), the following compounds were prepared:

2-(3-Benzamido-4-hydroxyphenyl)propionic acid, m.p. 189°–192°C.
2-(3-o-Chlorobenzamido-4-hydroxyphenyl)propionic acid, m.p. 150°–157°C.
2-(3-p-Chlorobenzamido-4-hydroxyphenyl)propionic acid, m.p. 209°–216°C.

On heating the foregoing compounds, there were obtained respectively:

2-(2-Phenyl-5-benzoxazolyl)propionic acid, m.p. 177°–178°C.,
2-(2-o-Chlorophenyl-5-benzoxazolyl)propionic acid, m.p. 102°–103°C.,
2-(2-p-Chlorophenyl-5-benzoxazolyl)propionic acid, m.p. 188°–190°C.

In the following Examples of pharmaceutical compositions of the present invention, the term "medicament" is used to indicate the compound 2-(2-p-chlorophenyl-5-benzoxazolyl) propionic acid. That compound may of course be replaced by any other active compound of formula I and the amount of medicament may be increased or decreased depending on the degree of activity of the medicament used.

EXAMPLE 28

Tablets each containing 100 mg of medicament are made as follows:

| Medicament | 100 mg |
| --- | --- |
| Potato starch | 38 mg |
| Lactose | 25 mg |
| Ethyl cellulose (as 20% solution in industrial alcohol) | 2 mg |
| Alginic acid | 7 mg |
| Magnesium stearate | 1 mg |
| Talc | 2 mg |
| Total | 175 mg |

The medicament, starch and lactose are passed through a No. 44 mesh B.S.S. sieve and mixed thoroughly. The solution of ethyl cellulose is mixed with the resultant powders which are then passed through a No. 12 mesh B.S.S. sieve. The granules produced are dried at 50°14 60°C. and then passed through a No. 16 mesh B.S.S. sieve. The alginic acid, magnesium stearate and talc, previously passed through a No. 60 mesh B.S.S. sieve, are added to the granules, mixed and compressed in a tabletting machine to yield tablets each weighing 175 mg.

EXAMPLE 29

Capsules each containing 200 mg of medicament are made as follows:

| Medicament | 200 mg |
| --- | --- |
| Lactose | 48 mg |
| Magnesium stearate | 2 mg |

The medicament, lactose and magnesium stearate are passed through a No. 44 mesh B.S.S. sieve and filled into hard gelatine capsules in 250 mg quantities.

EXAMPLE 30

Injection solutions each containing 100 mg of medicament per 5 ml solution are made as follows:

| Medicament | 100 mg |
| --- | --- |
| Sodium hydroxide (10% solution) | q.s. |
| Water for injection | to 5 ml |

The medicament is suspended in the water and the sodium hydroxide solution added drop by drop with stirring until the medicament is in solution. The pH of the solution is adjusted to between 8.0 and 8.5, the solution is sterilised by filtration through a bacteria-proof filter and filled into previously sterilised glass ampoules which are then hermetically sealed under aseptic conditions.

EXAMPLE 31

Suppositories each containing 250 mg of medicament are made as follows:

| Medicament | 250 mg |
| --- | --- |
| Theobroma Oil | to 2000 mg |

The medicament is passed through a No. 60 mesh B.S.S. sieve and suspended in the theobroma oil previously melted using the minimum of heat necessary. The mixture is then poured into a suppository mould of nominal 2 g capacity and allowed to cool.

We claim:

1. Pharmaceutical composition comprising an amount effective for treatment of inflammatory algesia and/or prepeticosis of a pharmacologically active compound in association with at least one pharmaceutically acceptable carrier therefor, said active compound being a compound of the formula:

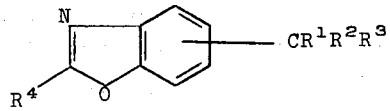

wherein the group —$CR^1R^2R^3$ is in the 5- or 6-position of the benzoxazole nucleus, wherein $R^4$ is cyclohexyl, furyl, thienyl, pyridyl, pyrazinyl, or phenyl or phenyl substituted in any available position by one or two substituents selected from halogen, nitro, amino, hydroxy, $C_1$–$C_4$ alkyl, $C_1$–$C_4$ alkoxy, $C_1$–$C_3$ alkyl-CO, $C_1$–$C_4$ alkyl sulphonyl or substituted in two adjacent positions by methylene- or ethylene-dioxy, $R^1$ and $R^2$ are independently hydrogen, methyl or ethyl and $R^3$ is:
  i. the group —$COOR^5$, where $R^5$ is $C_1$–$C_4$ alkyl
  ii. the group —CO—$R^6$ is —NHOH or $NH_2$; or
  iii. the group —$CH_2OR^9$ where $R^9$ is hydrogen or $C_1$–$C_4$ alkyl; or
  iv. the group —COOH or an alkali or alkaline earth metal, aluminum or ammonium salt thereof.

2. Composition according to claim 1, containing from 25 to 500 mg. of said active compound.

3. Composition according to claim 1, wherein said active compound is selected from:
  a. 2-(2-p-chlorophenyl-6-benzoxazolyl)propionic acid;
  b. 2-(2-p-chlorophenyl-5-benzoxazolyl)propionic acid;
  c. 2-(2-o-chlorophenyl-5-benzoxazolyl)propionic acid;
  d. 2-[2-(2,4-dichlorophenyl)-5-benzoxazolyl]propionic acid;
  e. 2-(2-p-fluorophenyl-5-benzoxazolyl)propionic acid;
  f. 2-(2-p-bromophenyl-5-benzoxazolyl)propionic acid;
  g. 2-(2-phenyl-5-benzoxazolyl)propionic acid;
  h. 2-(2-p-iodophenyl-5-benzoxazolyl)propionic acid;
  i. an alkali metal salt of compounds (a) to (h) above; and
  j. an $C_{1-4}$ alkyl ester of compounds (a) to (h) above.

* * * * *

UNITED STATES PATENT OFFICE
CERTIFICATE OF CORRECTION

PATENT NO. : 3,962,452
DATED : June 8, 1976
INVENTOR(S) : Delme Evans, etal.

It is certified that error appears in the above-identified patent and that said Letters Patent are hereby corrected as shown below:

Line 43, Column 23, after "50°", "14" should be -- - --, so as to read --50° - 60°C.--

Signed and Sealed this

Thirty-first Day of May 1977

[SEAL]

Attest:

RUTH C. MASON
*Attesting Officer*

C. MARSHALL DANN
*Commissioner of Patents and Trademarks*